United States Patent
Nam

(10) Patent No.: US 8,298,592 B2
(45) Date of Patent: Oct. 30, 2012

(54) HAIR GROWTH STIMULANTS ADN THE MANUFACTURING METHOD THEREOF

(75) Inventor: Jong Hyun Nam, Seoul (KR)

(73) Assignee: Jong Hyun Nam, Seoul (KR)

( * ) Notice: Subject to any disclaimer, the term of this patent is extended or adjusted under 35 U.S.C. 154(b) by 68 days.

(21) Appl. No.: 12/877,737

(22) Filed: Sep. 8, 2010

(65) Prior Publication Data

US 2010/0330209 A1    Dec. 30, 2010

Related U.S. Application Data

(62) Division of application No. 12/097,066, filed as application No. PCT/KR2006/000486 on Feb. 10, 2006, now abandoned.

(30) Foreign Application Priority Data

Dec. 5, 2005    (KR) .................. 10-2005-0121967

(51) Int. Cl.
*A61K 36/00* (2006.01)
*A61K 36/13* (2006.01)

(52) U.S. Cl. .............. 424/725.1; 424/770; 424/776

(58) Field of Classification Search .................. None
See application file for complete search history.

(56) References Cited

U.S. PATENT DOCUMENTS

| | | | |
|---|---|---|---|
| 3,086,909 A | | 4/1963 | Otsuki et al. |
| 4,626,433 A | * | 12/1986 | Gros .................. 424/682 |
| 5,466,453 A | * | 11/1995 | Uchida et al. ........... 424/735 |
| 5,494,667 A | | 2/1996 | Kabushiki |
| 5,750,107 A | | 5/1998 | Nomura |
| 2002/0155086 A1 | | 10/2002 | Verdun et al. |
| 2003/0082130 A1 | | 5/2003 | Verdun et al. |
| 2008/0299061 A1 | * | 12/2008 | Nam .................. 424/63 |

FOREIGN PATENT DOCUMENTS

| | | |
|---|---|---|
| CA | 1199276 | 1/1986 |
| CN | 1074832 | 8/1993 |
| CN | 1092670 | 9/1994 |
| CN | 1127129 | 7/1996 |
| CN | 1134813 | 11/1996 |
| CN | 1222389 | 7/1999 |
| CN | 1432378 | 7/2003 |
| CN | 1457872 | 11/2003 |
| CN | 1671405 | 9/2005 |
| JP | H03164811 A | 6/1990 |
| JP | 10045539 * | 2/1998 |
| JP | H1045539 A | 2/1998 |
| JP | 63091315 | 4/1998 |
| JP | 2004323480 | 11/2004 |
| KR | 10-1999-0068281 | 9/1999 |
| KR | 2001037953 | 5/2001 |
| KR | 10-2004-0009342 | 1/2004 |
| WO | WO-0152873 A1 | 7/2001 |
| WO | WO-2004-009108 | 1/2004 |
| ZA | 987083 | 8/1998 |

OTHER PUBLICATIONS

Web publication entitled "Classification of the Genus Pinus", 6 pages, downloaded from the web on May 30, 2011 from http://www.pinetum.org/Lovett/classification.htm.*

Aburjai et al., "Plants used in Cosmetics", Phytother. Res., Nov. 2003, 989-1000, 17, 9.

* cited by examiner

*Primary Examiner* — Christopher R. Tate
(74) *Attorney, Agent, or Firm* — IpHorgan Ltd.

(57) ABSTRACT

A hair growth stimulant having excellent hair growth stimulation and hair growth effects without any side effects, which contains a carbonized pine cone. The inventive hair growth stimulant has an excellent hair growth stimulation effect without causing any side effects or toxicity to the human body, while it can stimulate hair roots to greatly influence the growth of hair so as to prevent hair loss and white hair. Also, it can be provided in the form of creams or ointments having an excellent effect on hair growth stimulation, and thus can considerably shorten a treatment period. It can keep the anagen-stage hair by increasing the blood flow of the scalp, and it consists of a vegetable preparation, and so has no side effects to the human body. In addition, it can be used through smooth application to a head, and thus is easy to use.

19 Claims, No Drawings

HAIR GROWTH STIMULANTS ADN THE MANUFACTURING METHOD THEREOF

CROSS REFERENCE TO RELATED APPLICATIONS

This application is a divisional of U.S. application Ser. No. 12/097,066 filed on Jun. 12, 2008, which is a National Phase application of PCT/KR2006/00486, filed on Feb. 10, 2006, and which claims priority from Korean patent application number 10-2005-0121967, filed Dec. 12, 2005, the entire specifications of which are incorporated herein by reference.

BACKGROUND OF THE INVENTION

1. Technical Field

The present invention relates to a hair growth stimulant and a preparation method thereof, and a hair growth stimulant having excellent hair stimulation and hair growth effects without side effects or toxicity, which comprises a carbonized pine cone, as well as a preparation method thereof.

2. Background Art

So far as known, hair loss is caused by various factors, including a reduction in hair function by testosterone, a reduction in the metabolic function of the hair root, a reduction in the physiological function of a head, a reduction in regional cerebral blood flow that causes abnormal hair growth due to a reduction in the peripheral vascular blood flow of subcutaneous tissue of a head, nutritional deficiency, stresses, drug side effects, and genetic factors.

Hair or the skin plays an important role to show the function of human organs and the condition of the human body. Hair determines a beautiful effect in individuals and personal appearance or image, and at the present time, hair conditions are impaired due to nutritional deficiency, the excessive intake of instant food, etc.

Hair grows about 0.3-0.4 mm a day by an excess of blood, but white hair or hair loss conditions appear due to various environmental factors as described above.

Common men lose hair during the catagen and telogen stages after the anagen stage for 4~5 years, and women lose hair during the catagen and telogen stages after the anagen stage for 5~6 years.

Alopecias are divided according to the cause of hair loss into many kinds, including genetic alopecia, alopecia seborrhecia, alopecia areata, alopecia by nutritional deficiency, alopecia by drug side effects, alopecia by fungi, alopecia by insufficient adaptation to environmental changes, neurotic alopecia, etc.

However, in most of these alopecias, the scalp becomes warm in an initial stage and have inflammatory protrusions occurred thereon, so that hair becomes thin and loses elasticity while it falls out.

Commercially available hair growth stimulants include vasodilators such as carpronium chloride, minoxidil and various extracts, hormones for inhibiting testosterone action such as estrogen or estragiol, and testosterone activity inhibitors such as pentadecanoic acid or finasteride. Hormones for inhibiting testosterone and testosterone inhibitors have a problem of insufficient clinical effects or side effects of inhibiting male sexual function. Also, hair growth stimulant compositions containing various extracts cause a problem of skin abnormality upon application to the skin.

Developed and sold drugs for the treatment and prevention of alopecia include hair growth stimulants, such as a minoxidil preparation approved by USA FDA, and finasteride (proscar) for oral administration, inhibiting the action of 5-alpha-reductase to inhibit the production of dihydrotestosterone. However, these drugs are expensive and have problems in use, such as a reduction in effects when applied directly to the scalp, and side effects when administered orally.

Accordingly, there is a continued need for the development of a hair growth stimulant which has an excellent effect of preventing hair loss and is easy to use while not causing side effects, such as skin abnormality and the inhibition of male sexual function.

SUMMARY OF THE INVENTION

Accordingly, the present inventors have conducted studies to develop a hair growth stimulant which can maximize hair loss prevention and hair growth effects by completely removing follicular impurities and fatty materials, the main causes of hair loss, and rapidly regenerating follicular cells.

As a result, the present inventors have developed a hair growth stimulant that eliminates the use of hormones capable of causing side effects, contains a natural substance harmless to the human body while having good sensory feel, and shows surprising effects, thereby completing the present invention.

It is an object of the present invention to provide a hair growth stimulant having an excellent hair growth effect without causing side effects or toxicity to the human body, which is based on natural substances, a carbonized pine cone and an herbal medicinal extract, as well as a preparation method thereof.

To achieve the above object, the present invention provides a hair growth stimulant containing as active ingredients a carbonized pine cone and vegetable oil.

The hair growth stimulant according to the present invention can be prepared by mixing the carbonized pine cone and the vegetable oil at a weight ratio of 1:1 to 6:4.

The vegetable oil may be at least one selected from the group consisting of sesame oil, olive oil, *perilla* oil, coconut oil, castor oil, bean oil and seed oil.

The hair growth stimulant may additionally comprise at least one herbal medicinal extract selected from the group consisting of an apricot seed, an acorn, gromwell, a pomegranate, a pasque flower and licorice.

As the herbal medicinal extract, a solvent extract by extracting said herbal material with hot water, organic solvent or oil can be used.

The gromwell extract can be prepared by heating sesame oil at a temperature of 100-300° C. and adding and concentrating gromwell in the heated sesame oil in an amount of 10-30 wt % based on the weight of the sesame oil.

The pomegranate extract can be prepared by adding pomegranate in an amount of 5-25 wt % to sesame oil and storing the mixture at 30-50° C. for 1-30 days.

The pasque flower extract can be prepared by indirectly heating a pasque flower at a temperature of 100-300° C. and adding sesame oil in an amount of 80-90 wt % to the carbonized material.

The solvent extract can be used after dilution, concentration or drying.

The hair growth stimulant according to the present invention can be prepared by mixing the carbonized pine cone, the vegetable oil and the herbal medicinal extract with each other at a ratio of 1:1:1 to 3:4:3.

According to one embodiment of the present invention, the carbonized pine cone, the vegetable oil, the apricot seed extract, the acorn extract and the licorice extract can be at a mixing weight ratio of 10-70:10-50:5-20:5-20:10-15.

According to another embodiment of the present invention, the carbonized pine cone, the vegetable oil, the apricot seed extract, the acorn extract, the gromwell extract and licorice extract can be used at a mixing weight ratio of 10-70:5-40: 10-30:5-20:5~20:5-20.

Also, the hair growth stimulant according to the present invention may additionally comprise adjuvants such as a blood flow stimulant, a counter irritant, a follicle restorer, and anti-inflammatory and antibacterial agents.

The carbonized pine cones can be obtained by washing carefully selected pine cones with water, drying the washed material, and completing burning the dried material by heating in a closed container at a temperature of 100-300° C. for 1-8 hours.

In another aspect, the present invention provides a method for preparing a hair growth stimulant, comprising the steps of: preparing a carbonized pine cone; preparing sesame oil; mixing the carbonized pine cone and the sesame oil with each other; and adding an excipient to the mixture.

The inventive method for preparing the hair growth stimulant may additionally comprise the step of preparing an herbal medicinal extract.

The carbonized pine cone can be obtained by completely burning a pine cone in a closed container at 100-300° C. for 3-10 hours.

DETAILED DESCRIPTION OF THE PREFERRED EMBODIMENTS

The pine cone which is used as a main component in the present invention as described above is a pine seed growing at a pine tree. The pine tree is also called Sol, Chamsol, Songmok, Solnamoo, Sohorinamu in Korea. The pine tree is also called a red pine tree since its bark and a bud at the end of its shoot are red in color. In China, it is also called female pine, Yodong red pine, and short-leaf red pine. The pine tree is bifoliate, where two leaves form a couple. It is also called Isoosong, Ichimsong (denoting two-needle pine), Iripsong, etc. The scientific term of the pine tree is *Pinus densiflora* Siebold et Zuccarini. When the pine seed sprouts, cotyledons covered with the testa will come out above earth, and the number of the cotyledons is about 4 to 9 and is 6 in most cases. Pine leaves deviating the cotyledons form a couple and come out with one confronting the other and the bottom portion is in the vagina that is about 2 or 3 mm in size. The vagina is dark brown and is alive as long as the leaves live, without failing down. Meanwhile, there are female and male flowers in pine, which bloom in the last ten days of April and the first ten days of May. The male flower is elliptical and 4 to 9 mm in length. The end of the stamen spreads in the shape of the half moon and there are two anthers below filaments. There are two wings in pollen. Meanwhile, the female flower is hung 2 or 3 at the end of the branch. The initial shape is circular or elliptical and is about 5 mm in length and is light violet in color. This is a collection of a multitude of female flowers, which is called a cone. This is what is called a pine cone in the present invention. Mature pine cones consist of various scaly leaves, and in a scaly leaf, two ovules are in contact, which later on become a seed with two wings. Young cones in spring before pollination are called storbile or conelet in English, instead of cones. Scaly leaves of the pine cone is in contact with the axis of the pine cone helically, its end is fat and big, its exposed part is near the diamond shape, and there is a protrusion in its center. When the pine cone is mature, the gap between scaly leaves become bigger and the seeds are fallen apart and come flying out.

The pine cone that is a raw material for preparing the carbonized pine cone can be collected from various pine trees. Examples of pine trees from which the pine cone can be collected include forma aurescens, forma anguina, var *globosa*, forma pendula, forma aggregata, forma bi-aggergata, forma erecta, etc.

The sesame is an annual plant growing to a height of 90-150 cm and has short fuzz and long oval-shaped or willow leaf-like leaves that adhere while looking at each other. It has a soft eggplant-like color or a white color in summer while it contains seeds having colors varying depending on its varieties. The seeds are collected by cutting the stems in August or September when the fruits ripened, drying the cut stems in a bundle in the sunlight, shaking the dried stems to collect the seeds and removing foreign matter. The black seed is use as a drug, and the white seed is used as the raw material of oil. Oil squeezed from the dried seeds is used and this oil is slightly yellow in color and smells fragrant. It is miscible with ether, chloroform and petroleum ether and slightly dissolved in alcohol. Also, it hardens upon cooling at 0-5° C. Also, it has a specific gravity of about 0.9, a refractive index of about 1.5, an acid number of 2 or less, a saponification number of 188-195, and an iodine number of 103-116. Also, it contains glycerides such as oleic acid, linoleic acid, palmitic acid, stearic acid, arachidonic acid, lignoserinic acid. The non-saponified portions of the oil is present in an amount of 0.1-1.3% and include pytosterine, d-sesamine, sesamol, sesamoline, and vitamin E. Sesamol shows a red color by furfural and concentrated hydrochloric acid, and this reaction is used to identify sesame oil. The effects of sesame are widely known also in the prior medical books. Particularly, black sesame has plain properties and is sweet and innoxious (Dongeuibogam). Also, it increases vigor, grows fat, replenishes marrow and brain tissue, strengthens muscles and bones, and softens the five viscera (Bongchogangmok). Also, it builds up marrow, replenishes sperm, extends life span, and makes a face color look younger. The black sesame oil acts to increase blood platelet so as to rapidly coagulate blood. Accordingly, it is sometimes used against idiopathic thrombocytopenia, hemorrhagic thrombocytopenia, and hemorrhagic diseases.

The apricot seed is Armeniacae Semen that is a kind of a biosynthetic drug showing analgesic and anti-inflammatory effects.

The acorn is the fruit of *Quercus* Acutissima Carruthers belonging to the family Fagaceae and wildly in all the areas in Korea except for Pyungannamdo. It is distributed in Japan, China, Manchuria, and India, and it flowers in May and has a spherical fruit and a dish-shaped cupule and ripens in October. The acorn is characterized by containing 6-9% of tannin having a puckery taste, unlike other fruits. This tannin is known to have physiological actions such as antioxidant, antitumor, antiviral and antiallergic actions.

The gromwell is a perennial grass growing to a height of 30-70 cm and having strong fuzz. It has willow-like leaves that cross each other. In early summer, it blooms a five-branched white small flower at shoot ends and leaves which differentiate into seeds. Its root is gathered in autumn and dried in the sunlight. Its flower and root have a black reddish eggplant color. The root contains napthoquinone derivatives having a red color, for example, acetylshikonin, shikonin, isovalerylshikonin, β,β-dimethylacryl-shikonin, teracryl-konin, β-hydroxyisovaleryl-shikonin, α-methyl-n-butylshikonin, deoxyshikonin, and anhydroalkannin, and alkannan. Also, those found in the root include alkaloid, triterpensaponine, I-volnesitol, inositol, leutin, and nitrile glycoside. Its aerial parts contain phenolcarbonic acid. In addition, it has antibacterial or anti-inflammatory action.

The pomegranates are divided into a sweet family having a strong sweet taste and a sour family having a strong sour taste, and its fruit and skin all have a good effect on the prevention of hypertension and arterial sclerosis and an effect against women's diseases and a boil. Particularly, it shows an excellent effect against dysentery infection and contains volatile alkaloid and thus is used as a parasiticide, particularly as a taeniacide. Also, it contains citric acid promoting the decomposition of glucose, Vitamins (B1, B2, niacin) necessary to activate energy metabolism, and minerals having a close connection with most of physiological actions. Its leaf adheres to a long-oval fruit. Its flower has various colors, such as a red color, an eggplant color and a white color, and its fruit is round in shape and has a rough surface due to knob-like shapes present on the surface, and breaks upon ripening. The bark peeled from the stem and the root are sometimes used, and the more fresh the bark, the higher the alkaloid content. The root and stem bark alkaloids and ellagitannin, in which the alkaloids include pelletierine, iso-pelletierine, methyl iso-pelletierine (methyl isopiperidine), pseudopelletierine, and the like. The alkaloid content varies depending on seawater where the tree grows, and its varieties and parts, and the tannin consists of a glycoside-like linkage of ellagic acid and glucose. The ellagitannin will be converted into ellagic acid when decomposed in water. In addition, its tree bark contains betulic acid, and its fruit and leaf contain ursolic acid. Its bark contains mannitol and equimol. Its flower pigment punicin, and its seed contain oil based on a glyceride of punicic acid. Also, its fruit juice contains invert sugar and organic acid. In addition, its fruit skin contains viscous liquid and tannin.

The pasque flower is a perennial grass and contains anemonin and tannin. The anemonin is contained in a fresh root in the form of protoanemonin which is polymerized in air to form anemonin.

The licorice is a perennial grass belonging to the family legumiinosae, and its outer bark has a reddish brown color to a dark brown color. It is distributed in the northeastern region of China, a Mongol region, USA, and the continent of Africa, and its root and rhizome are used as medicinal herbs. Licorice extracted with distilled water, ethanol or ether is known to have an excellent antioxidant effect, and contains a large amount of flavonoids which can be separated into 30 kinds of compounds. The effects of licorice flavonoids, which have been found so far, include antioxidant effect, radical reducing effect, antibacterial effect, antiulcer effect, cough relief effect, antimutagenic effect, and antiviral effect. Glycyrrizine which is one of the typical components contained in the root of licorice is the sweet component of licorice and present as a white to lemon yellow crystal. In addition to a strong sweet taste, the glycyrrizine has various pharmacological effects.

The hair growth stimulant according to the present invention can be prepared by mixing the carbonized pine cone as a main component with vegetable oil. Also, the hair growth stimulant may additionally comprise an herbal medicinal extract obtained from the apricot seed, the acorn, the gromwell, the pomegranate, the pasque flower and the licorice, as well as an adjuvant, such as a blood flow stimulant, a counter irritant, a follicle restorer, and an anti-inflammatory and antibacterial agent.

The carbonized pine cone can be obtained by washing a carefully selected pine cone with water, drying the washed material, completely burning the dried pine cone by heating in a closed container at 100-300° C. for 3-10 hours, and then sieving the carbonized material through a 50-200 mesh sieve.

As the herbal medicinal extract, a solvent extract obtained by extracting an herbal medicinal material selected from among apricot seeds, acorns and licorice with hot water, organic solvent or oil can be used. Also, these solvent extracts may be used after dilution, concentration or drying. The extraction can be performed using a solvent at room temperature or elevated temperature. Alternatively, it can be performed using an extraction device such as soxhlet. The organic solvent used in the extraction process is not specifically limited and can be exemplified by known solvents, including lower alcohols such as methanol or ethanol, liquid polyhydric alcohols such as propylene glycol or 1,3-butylene glycol, and lower alkyl ester such as ethyl acetate. These solvents may be used alone or a mixture of two or more.

Preferably, a raw material selected from among the apricot seed, the acorn and the licorice is extracted at 60-120° C. for 1-8 hours and the extract is concentrated to 12-60 Brix at low temperatures.

According to one embodiment of the present invention, the gromwell extract can be prepared by heating sesame oil at a temperature of 100-300° C. and adding and concentrating the gromwell in the heated sesame oil in an amount of 10-30 wt % based on weight of the sesame.

According to one embodiment of the present invention, the pomegranate extract can be prepared by adding the pomegranate in an amount of 5-25 wt % to sesame oil and storing the mixture at a temperature of 30-50° C. for 1-30 days.

According to one embodiment of the present invention, the pasque flower extract can be prepared by indirectly heating the pasque flower at a temperature of 100-300° C. and adding sesame oil in an amount of 80-90 wt % to the resulting carbonized material.

As the vegetable oil, seed oil, such as sesame oil, olive oil, *perilla* oil, bean oil, grape seed oil, caster oil, and Cuscutae Semen oil.

According to one embodiment of the present invention, sesame oil is used as the vegetable oil.

As the sesame oil, black sesame oil or white sesame oil can be used. The sesame oil contains a large amount of an antioxidant, and thus does not degeneration, such as oxidation, even upon long-term storage, and contains larger amounts of essential fatty acids such as linolic acid, linoleic acid and arachidonic acid, compared to other oils. These essential fatty acids are known to prevent cell aging and white hair. Olive oil is produced in Mediterranean areas, such as Spain, Italy and Greece, and contains a large amount of a natural antioxidant substance.

Preferably, the inventive hair growth stimulant can be prepared by mixing the carbonized pine cone and the vegetable oil at a weight ratio of 1:1 to 6:4.

The hair growth stimulant according to the present invention can be prepared by mixing the carbonized pine cone, the vegetable oil and the herbal medicinal extract at a weight ratio of 1:1:1 to 3:4:3.

Also, the hair growth stimulant according to the present invention can be prepared by mixing the carbonized pine cone, the sesame oil, the apricot seed extract, the acorn extract and the licorice extract at a weight ratio of 10-70:10-50:5-20:5-20:10-15, but it is not limited thereto. By being prepared in this manner, the inventive hair growth stimulant can stimulate the health and growth of hair and can be prevented from oxidation.

Also, the inventive hair growth stimulant can stimulate the health and growth of hair and can be prevented from oxidation, by preparing the stimulant by mixing the carbonized pine cone, the sesame oil, the apricot seed extract, the acorn extract, the gromwell extract and the licorice extract at a weight ratio of 10-70:5-40:10-30:5~20:5-20:5~20, but it is not limited thereto.

Hair grows and falls out during a cycle consisting of the anagen, catagen and telogen stages. In this cycle, hair grows in the anagen state and stops to grow in the catagen stage so as to fall out. The hair growth stimulant according to the present invention acts to stimulate the fast growth of hair, to protect hair in the anagen stage and to make hair growing, by extending the catagen stage and supplying nutrients to hair in the telogen stage so as to restore the hair to the state of the initial anagen stage.

The hair growth stimulant according to the present invention can be formulated into any known preparations. For example, it can be formulated into preparations for local application, such as ointments or creams.

Also, the inventive hair growth stimulant can be used in the form of various cosmetics for use in hair or scalp, for example, hair lotion, hair cream, hair gel, hair rinse, and essence. Because the prior hair lotion, hair cream, hair gel and hair rinse contain no hair growth stimulant and provides merely a beauty effect, such cosmetics do not greatly help hair growing and to stimulate hair growth. However, if the hair growth stimulant according to the present invention is included in the compositions of various hair cosmetics, functional hair cosmetics can be prepared which can keep more glossy and fresh hair by supplying nutrients to not only the hairs of men and women having alpecia, to but also hair which lost elasticity due to environmental factors or stresses.

Moreover, the inventive hair growth stimulant may, if necessary, contain additives generally used in cosmetics or drugs, for example, a plant extract, an oily component, a surfactant, alcohols, fatty acids, a preservative, an antioxidant, a pigment, a fragrance, UV absorbing agent, a viscosity adjusting agent, a chelating agent, a pH adjusting agent, vitamins, and tablets, as long as these additives do not adversely affect the effects of the present invention.

The inventive ointment or cream preparation for the stimulation of hair growth can be prepared by suitably mixing organic acid, Vaseline and other excipients with a mixture of the carbonized pine cone and sesame oil and/or the herbal medicinal extract according to any general method for forming creams or ointments. The inventive ointment or cream preparation for the stimulation of hair growth preferably contains active ingredients, such as the carbonized pine cone, the vegetable oil and the herbal medicinal extract, in an amount of 0.1-30 wt %, and more preferably 5-20 wt %. If the content of the active ingredients is less than 0.1 wt %, it will have an insufficient effect on hair growth and stimulation, and if it exceeds 30 wt %, it will cause a difficulty in formulation and will not provide a great increase in effect resulting from an increased use thereof.

The pH of the inventive hair growth stimulant is preferably in a range of 4-7 in terms of safety to the human body, the absorption of components of the hair growth stimulant into the scalp, the prevention of decomposition, affinity for the skin, etc.

Hereinafter, the present invention will be described in more detail by Examples and Comparative Examples. It is to be understood, however, that these examples are for illustrative purpose only and are not construed to limit the scope of the present invention.

Example 1

Among the pine cones of a native kind of pine trees, pine cones having the desired size were carefully selected. The selected pine cones were washed with purified water and dried in the shade. As the pine cones were completely dried, 1000 g of the pine cones were placed in a completely closed container, and then completely burned by heating at about 300° C. for about 8 hours. Thereafter, the burned pine cones were left to stand for 2 hours to cool the pine cones, thus providing carbonized pine cones. The resulting carbonized pine cones were sieved through a 100-mesh sieve, thus obtaining about 800 g of carbonized pine cone powder.

Sesame was screened through a screening machine so as to eliminate foreign matter, and the screened sesame was washed and dried. After completion of the drying, it was roasted in a roaster at a temperature of about 160° C. until water was completely evaporated and just before smoke would be generated. The roasted sesame was pulverized with a pulverizer and squeezed to obtain sesame oil.

The carbonized pine cone and the sesame oil were mixed with each other at a weight ratio of 2:1, to which conventional excipients were then added such that mixture of the pine cone and the sesame oil was contained in an amount of 30 wt %. The resulting mixture was formulated as cream according to a conventional formulation method so as to prepare a hair growth stimulant.

Example 2

The procedure of Example 1 was repeated, except that the carbonized pine cone, the sesame oil, the apricot seed extract, the acorn extract, and the licorice extract were mixed with each other at a weight ratio of 30:40:10:10:10, respectively.

The apricot extract was obtained by adding purified water to a screened raw material, extracting the raw material at about 100° C. for 5 hours, and concentrating the extract to a solid content of about 75 BRIX at 55° C. According to this method, the acorn extract and the licorice extract were also obtained.

Example 3

The procedure of Example 2 was repeated, except that the carbonized pine cone, the sesame oil, the apricot seed extract, the acorn extract, and the licorice extract were mixed with each other at a weight ratio of 40:35:5:10:10.

Example 4

The procedure of Example 2 was repeated, except that the carbonated pine cone, the sesame oil, the apricot seed extract, the acorn extract, the licorice extract, and a gromwell extract were mixed with each other at a weight ratio of 30:30:10:10:10:10.

The gromwell extract was obtained by washing a screened raw material with purified water, heating sesame oil to a temperature of 250° C., and adding and concentrating the gromwell in the heated sesame oil for 3 hours.

Example 5

The procedure of Example 2 was repeated, except that the carbonated pine cone, the sesame oil, the apricot seed extract, the acorn extract, the licorice extract, and a pomegranate extract were mixed with each other at a weight ratio of 30:40:5:5:10:10.

The pomegranate extract was obtained by adding 15 wt % of a pomegranate to sesame oil and storing the mixture at a temperature of 40° C. for 20 days.

Example 6

The procedure of Example 2 was repeated, except that the carbonated pine cone, the sesame oil, the apricot seed extract, the acorn extract, the licorice extract, and a pasque flower extract were mixed with each other at a weight ratio of 40:30:10:5:5:10.

The pasque flower extract was prepared by indirectly heating a pasque flower at a temperature of 200° C. and then adding sesame oil in an amount of 85 wt % to the carbonized material.

Comparative Example 1

The procedure of Example 1 was repeated, except that the sesame oil, the apricot seed extract, the acorn extract, and the licorice extract were mixed with each other in the same amount.

Test Example 1

Test of Hair Growth Stimulation Effect (Comparison with Comparative Example)

On 20 male alopecia patients, each of the hair growth stimulants prepared in Examples 1 to 6 and Comparative Example 1 was applied on a scalp site that lost hair, 3 times a day, and the state of hair growth at the applied site was observed. The observation was performed starting from the start day of the test at 15-day intervals for 3 months. To evaluate the hair stimulation effect, the applied site was photographed with a digital camera, and the ratio (%) of area having recognized hair regeneration relative to the area of the scalp site that lost hair was calculated using image analysis software, and the results are shown in Table 1 below.

TABLE 1

| | 15 days | 30 days | 45 days | 60 days | 75 days | (Unit: %) 90 days |
|---|---|---|---|---|---|---|
| Example 1 | 10 | 15 | 20 | 25 | 30 | 50 |
| Example 2 | 10 | 20 | 30 | 40 | 60 | 80 |
| Example 3 | 10 | 15 | 20 | 25 | 30 | 50 |
| Example 4 | 10 | 15 | 30 | 50 | 65 | 75 |
| Example 5 | 10 | 20 | 25 | 35 | 60 | 70 |
| Example 6 | 10 | 15 | 25 | 45 | 60 | 75 |
| Comparative Example 1 | 2 | 4 | 8 | 10 | 12 | 12 |

Test Example 2

Test of Hair Growth Stimulation Effect

In order to examine whether the effect of the inventive hair growth stimulant is limited only to men and whether the effect is limited only to a young age group, the inventive hair growth stimulant was tested for 3 months on each of a first group consisting of 10 men and 10 women in their latter 30s and a second group consisting of 10 men and 10 women in their latter 40s. Specifically, the hair growth stimulation effect was tested in the same manner as in Test Example 1, except that the hair growth stimulant prepared in Example 2 was applied thinly on the scalp daily, the hair was washed in the morning, and the hair was washed with warm water, and then the hair growth stimulant was applied evenly on a scalp site that lost hair. The results are shown in Table 1 for the first group and in Table 3 for the second group.

As the clinical volunteers, those who have no experience of using a minoxidil preparation or various functional products 3 months before the start of the test and who have alopecia diseases, such as alopecia areata, telogen areata, cicatricial alopecia, alopecia seborrhecia, alopecia by nutritional deficiency, and alopecia nervosa, were selected.

TABLE 2

| | Hair growth rate of more than 80% (persons) | Hair growth rate of 20-80% (persons) |
|---|---|---|
| Men | 4 | 1 |
| Women | 4 | 1 |

TABLE 3

| | Hair growth rate of more than 80% (persons) | Hair growth rate of 20-80% (persons) |
|---|---|---|
| Men | 4 | 1 |
| Women | 4 | 1 |

Test Example 3

Safety Test

In the test of hair growth stimulation effect in Test Example 1, the state of the patient's skin just after applying the sample was observed and irritability was evaluated based on the following standards. The results are shown in Table 2.

○: no change,

□: showed slight erythema on the applied skin site.

X: showed clear erythema on the applied skin site.

TABLE 4

| | Irritability |
|---|---|
| Example 1 | ○ |
| Example 2 | ○ |
| Example 3 | ○ |
| Example 4 | ○ |
| Example 5 | ○ |
| Example 6 | ○ |
| Comparative Example 1 | ○ |

As can be seen in Table 1, the inventive hair growth stimulants of Examples 1 to 6 containing the carbonized pine cone showed an excellent hair growth stimulation effect compared to the preparation of Comparative Example 1 containing no carbonized pine cone, and could provide, after 12 weeks of application, a therapeutic effect of more than 80% on androgenetic alopecia and a therapeutic effect of more than 90% on alopecia areata. Also, as can be seen in Tables 2 and 3, the results obtained by testing the hair growth stimulant prepared in Example 2 on men and women in their latter 30s and 40s showed that persons having a hair growth effect of more than 80% exceeded 80% of the whole test subjects, and the remaining persons all showed a hair growth effect.

Furthermore, as can be seen in Table 4, all the preparations of Examples to 6 were not irritable to the skin.

Accordingly, the inventive hair growth stimulant can be used as an agent for treating alopecia, and if it is used in other cosmetic compositions associated with hair, it can provide a function capable of making hair more glossy and elastic, even upon use by a general person.

INDUSTRIAL APPLICABILITY

As described above, the hair growth stimulant according to the present invention has an excellent hair growth stimulation effect without causing any side effects or toxicity to the human body, while it can stimulate hair roots to greatly influence the growth of hair so as to prevent hair loss and white hair. Also, it can be provided in the form of creams or ointments having an excellent effect on hair growth stimulation, and thus considerably shorten a treatment period. Also, it can keep the anagen-stage hair by increasing the blood flow of the scalp, and it consists of a vegetable preparation having excellent effects on hair growth stimulation for stimulating the regrowth of hair in the telogen stage and on hair growth, and has no side effects on the human body. In addition, it can be used through smooth application to a head, and thus is easy to use.

What is claimed is:

1. A method for stimulating hair growth comprising the step of applying onto a scalp of a subject in need thereof a hair growth stimulant having as active ingredients, a carbonized *Pinus densiflora* cone, vegetable oil, and herbal medicinal extracts consisting of apricot seed extract, acorn extract, and licorice extract, wherein the carbonized *Pinus densiflora* cone, the vegetable oil, the apricot seed extract, the acorn extract and the licorice extract are present as a mixture therein within a weight ratio of 10-70:10-50:5-20:5-20:10-15.

2. The method of claim 1 wherein the vegetable oil is seed oil.

3. The method of claim 1 wherein the vegetable oil is at least one selected from the group consisting of sesame oil, olive oil, perilla oil, coconut oil, castor oil, bean oil and Cuscutae Semen oil.

4. The method of claim 1 wherein the herbal medicinal extracts are solvent extracts prepared by extracting each of the herbal materials with hot water, organic solvent or oil.

5. The method claim 4 wherein the solvent extracts are used after dilution, concentration or drying.

6. The method of claim 1 wherein the carbonized *Pinus densiflora* cone is obtained by washing a screened *Pinus densiflora* cone with water, drying the washed material, and completely burning the dried material by heating in a closed container at a temperature of 100-300° C.

7. The method of claim 1 wherein the hair growth stimulant additionally consists of at least one adjuvant selected from the group consisting of a blood flow stimulant, a counter irritant, a follicle restorer, and an anti-inflammatory and antibacterial agent.

8. The method claim 1 wherein the hair growth stimulant is in the form of a preparation for local application, hair lotion, hair cream, hair gel, hair rinse or essence.

9. The method of claim 1 wherein the hair growth stimulant preparation of local application is in the form of ointments or creams.

10. A method for stimulating hair growth comprising the step of applying onto a scalp of a subject in need thereof a hair growth stimulant having as active ingredients, a carbonized *Pinus densiflora* cone, vegetable oil, and herbal medicinal extracts consisting of apricot seed extract, acorn extract, gromwell extract, and licorice extract, and wherein the carbonized *Pinus densiflora* cone, the vegetable oil, the apricot seed extract, the acorn extract, the gromwell extract and licorice extract are present as a mixture therein within a weight ratio of 10-70:5-40:10-30: 5-20:5-20:5-20.

11. The method of claim 10 wherein the vegetable oil is seed oil.

12. The method of claim 10 wherein the vegetable oil is at least one selected from the group consisting of sesame oil, olive oil, perilla oil, coconut oil, castor oil, bean oil and Cuscutae Semen oil.

13. The method of claim 10 wherein the herbal medicinal extracts are solvent extracts prepared by extracting each of the herbal materials with hot water, organic solvent or oil.

14. The method claim 13 wherein the solvent extracts are used after dilution, concentration or drying.

15. The method of claim 10 wherein the gromwell extract is prepared by heating sesame oil to a temperature of 100-300° C. and then adding 10-30 wt % of the gromwell to the heated sesame oil.

16. The method of claim 10 wherein the carbonized *Pinus densiflora* cone is obtained by washing a screened *Pinus densiflora* cone with water, drying the washed material, and completely burning the dried material by heating in a closed container at a temperature of 100-300° C.

17. The method of claim 10 wherein the hair growth stimulant additionally consists of at least one adjuvant selected from he group consisting of a blood flow stimulant, a counter irritant, a follicle restorer, and an anti-inflammatory and antibacterial agent.

18. The method claim 10 wherein the hair growth stimulant is in the form of a preparation for local application, hair lotion, hair cream, hair gel, hair rinse or essence.

19. The method of claim 10 wherein the hair growth stimulant preparation of local application is in the form of ointments or creams.

* * * * *

UNITED STATES PATENT AND TRADEMARK OFFICE
CERTIFICATE OF CORRECTION

| | | |
|---|---|---|
| PATENT NO. | : 8,298,592 B2 | |
| APPLICATION NO. | : 12/877737 | |
| DATED | : October 30, 2012 | |
| INVENTOR(S) | : Jong Hyun Nam | |

It is certified that error appears in the above-identified patent and that said Letters Patent is hereby corrected as shown below:

Title Page, Item (54) and at Column 1, lines 1 and 2, in the title of invention, the title is corrected to read "HAIR GROWTH STIMULANTS AND THE MANUFACTURING METHOD THEREOF".

Title Page, Item (30) Foreign Application Priority Data, the date is corrected to read "Dec. 12, 2005".

Signed and Sealed this
Fifteenth Day of January, 2013

David J. Kappos
*Director of the United States Patent and Trademark Office*